United States Patent [19]

Chavin et al.

[11] Patent Number: 4,495,175

[45] Date of Patent: Jan. 22, 1985

[54] PREPARATION OF HIGHLY PURIFIED HUMAN ANTIHEMOPHILIC FACTOR

[75] Inventors: Stephen I. Chavin; Philip J. Fay, both of Rochester, N.Y.

[73] Assignee: University of Rochester, Rochester, N.Y.

[21] Appl. No.: 405,456

[22] Filed: Aug. 5, 1982

[51] Int. Cl.$^3$ .................... A61K 35/16; C07G 7/00
[52] U.S. Cl. ................................ 424/101; 260/112 R
[58] Field of Search .................. 424/101; 260/112 B, 260/112 R

[56] References Cited

U.S. PATENT DOCUMENTS

| | | | |
|---|---|---|---|
| 4,188,318 | 2/1980 | Shanbrom | 424/101 |
| 4,278,594 | 7/1981 | Amrani | 424/101 |
| 4,361,509 | 11/1982 | Zimmerman et al. | 260/112 B |
| 4,383,989 | 5/1983 | Rock | 424/101 |

OTHER PUBLICATIONS

Bolhuis et al.—Chem. Abst. vol. 92 (1980), p. 36359n.
Niiya—Chem. Abst. vol. 89 (1978), p. 193,473a.
Vehar et al.—Chem. Abst. vol. 92 (1980), p. 90,181m.
Kang et al.—Chem. Abst. vol. 92 (1980), p. 176730b.
Kimura et al.—Chem. Abst. vol. 95 (1981) p. 130281q.
Vukovich et al.—Chem. Abst. vol. 94 (1981) p. 2516n.

Primary Examiner—Sam Rosen
Attorney, Agent, or Firm—David J. Aston; Theodore J. Leitereg

[57] ABSTRACT

Highly purified, biologically active Human Antihemophilic Factor (AHF) preparations are prepared having specific activities of about 4000–8000 units per milligram of AHF. In the method of preparation an AHF concentrate, prepared by fractionation of plasma to partially remove fibrinogen, fibronectin and other plasma components is subjected to a separation on the basis of Stokes' radius to separate AHF from the bulk of remaining proteins in the AHF concentrate. The pooled fractions containing AHF activity are concentrated by precipitation with ammonium sulfate, sodium sulfate, etc., by diafiltration, by PEG addition, or the like. The concentrate, is solubilized or equilibrated in an aqueous medium and treated to change the effective Stokes' radius of the AHF to an apparently low value and then subjected to a separation from the concentrate. The AHF pool from above is treated to remove cations by dialysis against an appropriate buffer of lower ionic strength and chromatographed on an anion-exchange medium. The AHF fraction from the above chromatography, is a highly purified AHF preparation.

10 Claims, 5 Drawing Figures

PREPARATION OF HIGHLY PURIFIED HUMAN ANTIHEMOPHILIC FACTOR

BACKGROUND OF THE INVENTION

1. Field of the Invnention

This invention relates to and has among its objects the provision of novel methods for the preparation of highly-purified human Antihemophilic Factor preparations. Further objects of the invention will be evident from the following description wherein parts and percentages are by weight unless otherwise specified.

2. Description of the Prior Art

It is known that the clotting of human blood is a complicated process, involving a series of reactions mediated by 13 different factors. It also is well know that a cause of hemophilia is the inability of the afflicted individual to synthesize one of these factors, known variously as antihemophilic factor, AHF, AHG, Factor VIII or Factor VIII C, in amounts sufficient to support adequate clotting. About 40 percent of hemophiliacs have no ability to synthesize AHF, while the others have diminished ability. Dried preparations of AHF concentrate are sold commercially for administration to hemophiliacs for treatment of bleeding or in advance of surgery. The AHF concentrate is obtained from plasma from human donors, through the use of know techniques. At the time of use, the dried concentrate is dissolved in sterile water, and the resulting solution is administered intravenously.

The usual commercial AHF preparation is not pure AHF. Rather, it is an AHF-enriched fraction obtained from plasma and contains other components. It is desirable that the AHF concentrate be as pure as possible, but further improvements in purity through modification of the procedure for isolating AHF from plasma have not been practically feasible due to the difficulty of separating plasma components. AHF is quite difficult to separate and purify because of its low content in the plasma and the instability of its activity. The known AHF concentrates are prepared from fraction I separated from plasma by means of Cohn's ethanol fractionation method or from the cryoprecipitate obtained by freezing a plasma and then thawing it at a low temperature. However, they are all crude products of low purity and contain a large quantity of fibrinogen. If given in large or frequently repeated doses, they may make the state of the patient quite dangerous clinically, bringing an excessively overloaded fibrinogen content in the circulating system. Moreover, it is difficult to determine their accurate dose because of the deviation in the activity in each preparation. For the above-mentioned reasons, the current trend is towards the development of a highly purified, highly concentrated AHF preparation from a large quantity of pooled plasma. The high potency AHF concentrates hitherto disclosed are generally produced by first preparing crude fractions of AHF such as Cohn's fraction I or cryoprecipitate.

The prior art of AHF concentrate fractionation has demonstrated the the concentrate can be separated from fibrinogen and other proteins by column chromatography, polyethylene glycol (PEG) of polypropylene glycol (PPG) precipitation, glycine precipitation (or with other amino acids), as well as alcohol precipitation. British Pat. No. 1,507,198 and U.S. Pat. No. 3,973,002 utilize pH and temperature adjustments to result in some purification of an AHF concentrate to give low potency preparations of intermediate purity. The process described in these patents utilize a fraction extracted from the cryoprecipitate rather than cryoprecipitate itself. Furthermore, fractionation stops after one cycle of pH and cooling adjustment. Others have also recognized the effect of using one cycle of pH and cooling adjustment (J. K. Smith et al, *Transfusion* 19, 229-306, [1979]).

The compositions of AHF obtained by the processes discussed above are of relatively low concentration (of the order of about 5 to 15 units of AHF activity per ml) and low purity (less than 1 unit AHF activity per mg protein).

Polyethylene glycol fractionation and glycine-precipitated fractionation to yield AHF concentrates have been described in U.S. Pat. Nos. 3,415,804; 3,682,881; 3,770,631; 4,027,013; 3,839,314; 4,069,216; 3,631,018; 3,652,530; 4,073,886; and 4,085,095.

Kisker (*Thromb. Diath. Haemorrhagica*, 17, 381 [1967]), as well as Penick and Brinkhouse (*Amer. J. Med. Sciences*, 232, 434 [1956]), have pointed out in their papers, in the preparative process of such high potency AHF concentrates, particularly in the course of separating and purifying AHF the co-existing prothrombin complex and active forms of its constitutive factors, such as IIa, Xa and the like, are markedly detrimental to the stability of AHF and sometimes irreversibly injure the latter to inactivate it. In order to improve stability, yield and solubility of AHF, therefore, it is quite important and essentially necessary to inactivate or eliminate these instabilization factors at the earliest stage of the separation-purification step. Methods for inactivating said instabilization factors have been disclosed in, for example, U.S. Pat. No. 3,803,115. It has also been disclosed that said instabilization factors can be removed by the use of an adsorbent such as aluminum hydroxide, magnesium hydroxide, barium carbonate, barium sulfate, rivanol (6,9-diamino-2-ethoxyacridine lactate), ion-exchange resin (Amberlite IRC-50), glycine ethyl ester or the like (Bidwell, E. et al, *Brit. J. Haemat.*, 13, 568 [1967]; Soulier, J. P. et al, *Presse med.*, 72, 1223 [1964]; Surgenor, P. M. et al, *J. Phys. Colloid Chem.*, 55, 94 [1951]; Hoag, M. S. et al, *J. Clin Invest.*, 39, 554 [1960). Among them, aluminum hydroxide is known to be relatively good adsorbent of said instabilization factors and therefore has been used most frequently (U.S. Pat. No. 4,170,639). DEAE-crosslinked dextran has also been used to adsorb and remove the prothrombin complex (U.S. Pat. No. 4,093,608).

As mentioned above, the AHF concentrates obtained by the prior art processes discussed above are relatively low specific activity, namely about one unit or less of AHF activity per milligram (mg) of protein, one of the undesirable impurities being denatured AHF. U.S. Pat. Nos. 4,289,691 and 4,302,445 disclose processes for preparing AHF preparations having a specific activity of AHF activity of 1–3 units per mg of protein, and U.S. Pat. No. 4,294,826 describes a method for preparing human AHF having a specific activity of about 1–10 units of AHF activity per mg.

SUMMARY OF THE INVENTION

The method of the present invention provides highly purified, biologically active human AHF preparations. In the present method a concentrate containing AHF of intermediate purity, such as a commercial AHF preparation is prepared by fractionation of human blood plasma. The concentrate containing AHF is subjected to a separation on the basis of Stokes' radius to separate AHF from the bulk of proteins in the AHF concentrate. The pooled fractions from above containing AHF activity are concentrated, such as by precipitation by addition of ammonium sulfate, sodium sulfate, etc., by diafiltration, PEG addition, or the like. The concentrate is subsequently solubilized or equilibrated in an aqueous medium and treated to change the effective Stokes' radius of the AHF molecule to an apparently low value and then subjected to a separation on the basis of Stokes' radius to further separate AHF from the concentrate. The separated AHF is treated to remove cations by dialysis and chromatographed on an anion exchange medium to give a highly purified AHF preparation.

The human AHF preparations produced by the method of the invention have about 4,000–8000 units of AHF (procoagulant) activity per mg of protein (one unit of activity is that found in 1 ml of normal human plasma). The product having at least about 4,000 units of AHF activity per mg of protein appears to be homogeneous and have a molecular weight of 200,000–400,000 daltons by High Performance Liquid Chromatography (HPLC).

The primary advantage of the present invention is that for the first time a human AHF preparation of high purity and high activity is obtainable. As mentioned above the preparations of the invention are homogenous thus being essentially free of fibrinogen, fibronectin, von Willebrand's protein, Vitamin K-dependent coagulation factors, and other undesirable or destabilizing enzymes or proteins.

The improved process of the invention has the advantage of producing the above human preparation, which has heretofore been unavailable. All molecules of AHF in the present preparation can be cleaved by thrombin, an indication that AHF is in its native (i.e. non-destabilized) state.

DESCRIPTION OF THE PREFERRED EMBODIMENTS

Figure 1:
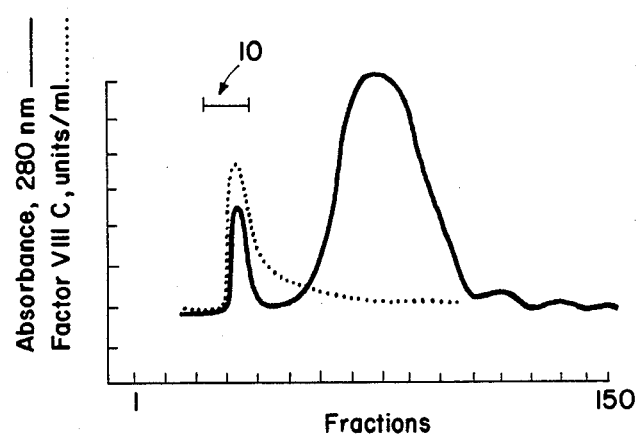
FIGS. 1–4 are depictions of the chromatographic separations of AHF (Factor VIII C) in the steps of the method of the invention.

The starting material of the present invention is a concentrate of AHF obtained from human blood plasma, such as a commercially available AHF preparation. According to standard procedure, frozen (at −20° C. or less) human blood plasma is obtained from a plasma collection center. The frozen plasma is treated to give a concentrate of AHF; for instance frozen plasma may be held at a temperature sufficient to produce a cryoprecipitate or treated with ethanol to give Cohn Fraction I. The AHF concentrate is separated from the pooled plasma by conventional techniques, such as centrifugation for cryoprecipitate.

The concentrate of AHF is next treated by known techniques to totally or partially remove other clotting proteins, such as prothrombin complex proteins, fibrinogen, albumin, and other proteins and to further concentrate the AHF. Removal of the above proteins may be accomplished according to known methods such as those described in the aforementioned patents, the disclosures of which are incorporated herein by reference. For example, the above proteins can be removed from a cryoprecipitate concentrate containing AHF by dissolving the cryoprecipitate in an aqueous medium, adding aluminum hydroxide to precipitate unwanted proteins, treating to adjust pH and salt concentration, and ultrafiltering to yield a concentrate of AHF with substantial reduction of the prothrombin complex proteins, fibrinogen, albumin, and the like. Alternately or in addition, the above proteins may be removed from the cryoprecipitate concentrate of AHF by polyethylene glycol and/or glycine precipitation.

The so-prepared concentrate of AHF may be treated to reduce its content of water, either partially or totally, by ultrafiltration, lyophilization, or a combination of both.

The concentrate of AHF is subjected to a separation on the basis of Stokes' radius wherein proteins of lower molecular weight are separated from AHF, which exhibits an apparently high Stokes' radius. The above separation may be accomplished in a variety of ways such as subjecting the AHF concentrate to gel permeation chromatography on cross-linked agarose (such as Biogel A-15 m or Sepharose CL-4B) or cross-linked polyacrylamide or to a controlled pore size glass bead treatment or to sucrose density gradient ultrafiltration. All of the above techniques are well-known in the art. Preferably, the AHF concentrate is subjected to gel permeation chromatography on, for example, cross-linked agarose or polyacrylamide. After equilibration on the chromatography medium, AHF is eluted with a buffered salt solution having an ionic strength of about 0.1–0.4 and a pH of about 6.0–7.5.

The fractions containing the eluted AHF from above are pooled and the pool is concentrated by techniques known in the art such as precipitation with ammonium sulfate, sodium sulfate, etc., by diafiltration, by PEG addition, or the like. For example, the AHF pool may be treated with ammonium sulfate (30–40%, weight/volume) to precipitate AHF. The AHF, after concentration, is dissolved or equilibrated in an aqueous salt buffer of pH about 6.0–7.5 and ionic strength about 0.1–0.4. If a salt such as ammonium sulfate was added in the course of concentration of the AHF pool, such salt is removed prior to the next step by known techniques such as dialysis, diafiltration, and the like.

Next, the AHF concentrate is treated to change the effective Stokes' radius of the AHF molecule to an apparently low value. To this end one may add a source of divalent cations such as calcium or magnesium wherein about 5–10 parts by volume of protein solution with 1 part of a solution about 1–3 M in divalent cation is employed per part by volume of AHF concentrate. The above mentioned reduction in Stokes' radius can also be accomplished by attaining a high ionic strength in solutions of AHF (e.g. about 1–4 M with sodium chloride) or the incubation of AHF with about 0.01–0.001 parts of thrombin per part of AHF concentrate (in units) (Leon W. Hoyer, Hemophilia and Hemostasis, "The Factor VIII Complex: Structure & Function", Alan R. Liss, Inc., pg. 7, [1981]).

Following reduction in Stokes' radius of the AHF molecule, the AHF concentrate is treated to remove divalent cations by known procedures such as dialysis or diafiltration and then is subjected to a separation on the basis of Stokes' radius by any of the means described above. Preferably, the AHF concentrate is subjected to gel permeation chromatography on cross-linked agarose or polyacrylamide, chromatographic medium equilibrated and eluted with a buffered salt solution having an ionic strength of about 0.1–0.4 and a pH of about 6.0–7.5.

The eluted fractions containing AHF activity are pooled and optionally concentrated by reduction of water content. To this end the pooled fractions may be concentrated by techniques known in the art such as dialysis, diafiltration, etc. The fractions may be immersed, in for example, solid PEG 20,000 in order to extract water from the solution within a dialysis container. The concentrated material is treated to remove divalent cations by dialysis, diafiltration, or the like, against a buffer at a pH of about 6.0–7.5.

Following the above concentration steps, the function containing AHF activity is subjected to chromatography on an anion exchange medium such as quaternary aminoethyl (QAE) cellulose, diethylaminoethyl (DEAE) cellulose, or similar anion exchanger.

The chromatographic medium is washed with a buffered aqueous solution having an ionic strength sufficient to remove unbound protein but not AHF, i.e., 0–0.2 (0–0.2 M sodium chloride, and the like). Finally the chromatographic medium is eluted with an aqueous solution having an ionic strength sufficient to elute AHF, i.e., about 0.2–0.6 (e.g. 0.2–0.6 M sodium chloride, and the like) to give fractions containing AHF, which are then pooled.

The pooled fractions from the above chromatography contain AHF having a specific activity of at least about 4000 AHF units per mg of protein and represent a substantially homogeneous preparation on ion exchange chromatography on QAE cellulose and sodium dodecyl sulfate (SDS) polyacrylamide gel electrophoresis (Laemmli). Such a product has heretofor, not been described, disclosed, or suggested by the prior art. Consequently, the pooled fractions constitute a concentrated AHF preparation purified at least about 350,000-fold over that found in plasma; it may be sterile filtered and lyophilized.

The pooled fractions from above may optionally be subjected to HPLC under non-denaturing conditions. For this purpose conventional HPLC apparatus may be employed and the elution of AHF accomplished in a standard manner based on Stokes' radius.

The fractions containing AHF are pooled and represent a 10% yield of product; the AHF has a specific activity of at least about 4,000 AHF units per mg of protein. The fraction may be sterile filtered and treated to reduce its water content either by ultrafiltration, lyophilization or combinations thereof. The AHF preparation exhibits homogeneity by HPLC and SDS polyacrylamide gel electrophoresis (PAGE) (Laemmli). Thus, the AHF preparation is essentially homogeneous and essentially free (i.e., contains less than about 1% combined of non-AHF proteins) of Factors II, VII, IX, X, fibrinogen, albumin, fibronectin, von Willebrand factor, and has essentially no activity in a non-activated partial thromboplastin time assay indicating that the purified protein essentially does not contain activated clotting factors circumventing the AHF dependent step in the clotting cascade.

The AHF preparations of the invention, in addition to having the ability to correct the clotting defect in hemophilic plasma, also exhibit the following characteristics:

(a) The biological activity is increased, and the putative polypeptide chain is altered, following treatment with thrombin. The purified protein can be activated by treatment of thrombin to give 4–20 fold increase in AHF activity.

(b) The biological activity can be blocked by the inhibitors against AHF which are found in certain patients with classical hemophilia. When mixed with a several fold excess (unit:unit) of AHF inhibitor, between 95 and 99% of the measurable AHF activity can be abolished.

(c) The purified native AHF has an elution volume corresponding to a molecular weight of 200–400,000 daltons. After reduction and SDS PAGE, there is a single polypeptide chain with an apparent molecular weight of about 100,000. Following incubation with thrombin, virtually all of the 100,000 polypeptide disappears and is replaced by a single broad band with a molecular weight of 75,000. No additional bands with lower molecular weights are seen.

(d) The purified AHF appears to be substantially free from significant protease activity, and from essentially all other plasma proteins.

(e) The purified AHF is substantially free from AHF antigen (Factor VIII:C Ag). The ratio of AHF:AHF antigen is usually about 50:1 or greater, usually within the range of about 50:1–150:1.

The amino acid composition of the human AHF preparation of the invention is given in Table 1.

TABLE 1

| Human AHF Amino Acid Composition | |
|---|---|
| Residue | No. of Residues per 100,000 Molecular Weight Sub-Unit |
| Cysteic Acid | 13 |
| Aspartic Acid | 65 |
| Threonine | 37 |
| Serine | 111 |
| Glutamic Acid | 110 |
| Proline | 30 |
| Glycine | 157 |
| Alanine | 50 |
| Methionine Sulfoxide or Carboxylmethyl Cysteine | 10 |
| Isoleucine | 24 |
| Leucine | 47 |
| Tyrosine | 23 |
| Phenylalanine | 22 |
| Histidine | 17 |
| Lysine | 45 |
| Arginine | 26 |
| Total Residues = | 833 |

Tryptophan was not detected in the system.
The identification of oxidyzed derivatives was tentative because these same residues were detected before and after oxidation.
No methionine or half-cystine was detected.

EXAMPLE

The invention is further demonstrated by the following illustrative examples.

Assays

1. Clotting Assays. AHF was measured by a one-stage clotting assay, using a substrate plasma from a patient with severe AHF deficiency (less than 1% AHF), and using a Fibrometer ® to determine the clotting time. One unit of AHF was defined as the amount in 1 ml of pooled normal human plasma. (Langdell et al, *J. Lab. Clin. Med.*, 41, 637–644, 1953.

2. Protein estimations were made using a Gilford 250 spectrophotometer. All samples were read at 280 nm and 320 nm, and the absorbance corrected for light scattering by the following formula.

$$A_{280\ corrected} = A_{280\ uncorrected} - 1.7\ (A_{320})$$

A mean $A_{1\ cm}^{1\%}$ of 10.0 was assumed for calculations of specific activity.

(3) Polyacrylamide gel electrophoresis. Sodium dodecyl sulfate-polyacrylamide gel electrophoresis was performed according to O'Farrell employing a 4.5% stacking gel with 6% separating gel. Electrophoresis was at 25 mA for four hours. Polyacrylamide gel electrophoresis under nondenaturing conditions employed a 5% gel and 25 mM tris and 192 mM glycine, pH 8.3. Electrophoresis was at 250 volts for three hours at 4° C. (O'Farrell, *J. Biol. Chem.*, 250, 4007–4012 1975). Gels were stained for protein using a silver nitrate. Protein was eluted from the unstained gel by slicing at 5 mm intervals and adding each slice to 0.3 ml of 50 mM Tris-hydrochloride, pH 7.0, 150 mM NaCl and 200 microgram/ml ovalbumin. The mixture was incubated at 4° C. for 2-3 hours and assayed for AHF procoagulant activity as described above.

(4) Factor VIII:C Ag Assay. The procedure of Reisner et al was followed. The antibody was kindly provided by Howard Reisner. (Reisner et al, *Thromb. Research*, 14, 135-239, 1979).

(5) Inhibition of AHF Activity. This was measured by mixing 1 volume of sample containing AHF with an equal volume of human plasma containing inhibitor to AHF. The concentration of inhibitor was always several fold in excess of the AHF concentration. After incubation for the time indicated, the residual AHF was assayed.

(6) Thrombin Activation of AHF. (Switzer et al, *J. Biol. Chem.*, 225, 10606-10611, 1980).

(7) von Willebrand Protein Assay. (Voller et al, *Bull World Health Organ.*, 53, 55-63, 1976).

(8) Silver Stain. (Merrill et al, *Science*, 211, 1437-1438, 1980).

EXAMPLE

Purification of AHF

The starting material was AHF therapeutic concentrate (Koate ®) from Cutter Laboratories, Inc.

(1) Referring to FIG. 1 gel permeation chromatography was carried out on Biogel A-15 m (Bio Rad Laboratories, 100-200 mesh) in a column 2.6×90 cm with $CaCl_2$ (1 mM), sodium citrate (5 mM), 0.135 M NaCl, 5% dextrose, 0.1% sodium azide at pH 7.35 and at ambient temperature as the eluant. The fractions containing the highest concentrations of AHF were pooled (10) and concentrated by precipitation with 40% w/v ammonium sulfate. In preparation for the next step, the precipitate was dissolved in 50 mM imidazole buffer at pH 7.0 containing 150 mM NaCl and dialyzed to remove residual ammonium sulfate.

Figure 2:
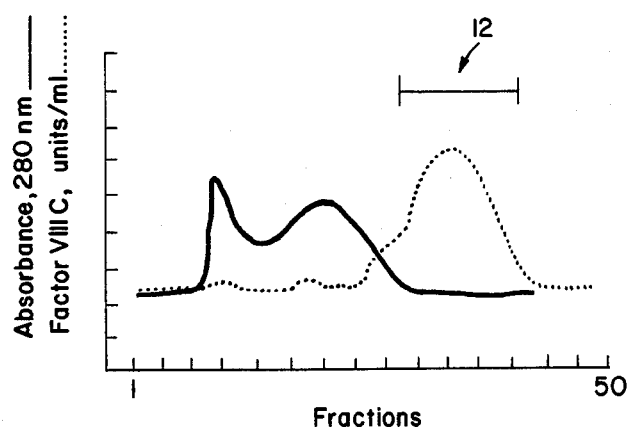

(2) The dialyzed sample from 1 above was made 250 mM in $CaCl_2$ by mixing 1 volume of 2.5 M $CaCl_2$ with 9 volumes of protein solution. The sample was then chromatographed on a 2×100 cm glass column of Sepharose 4B-CL previously equilibrated with the same buffer. The elution medium was a 50 mM imidazole buffer at pH 7.0 containing 50 mM NaCl and 0.25 M $CaCl_2$. Referring to FIG. 2, area 12 represents the fractions containing AHF activity, which were pooled.

Figure 3:
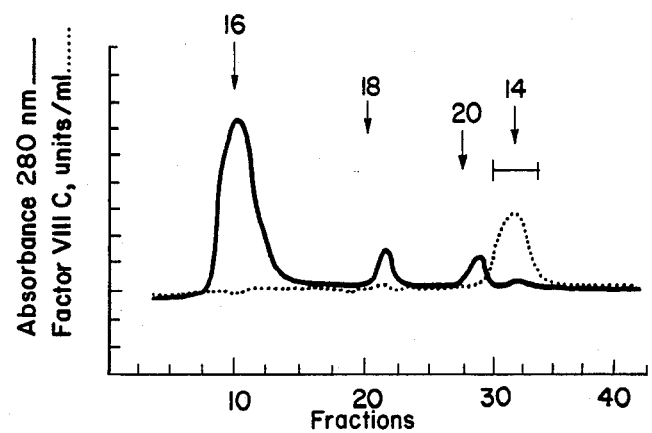

(3) The AHF pool (12) from the previous step was concentrated by placing the pool in a dialysis bag and immersing the bag in solid PEG-20,000. The concentrated sample was then dialyzed against 50 mM imidazole buffer pH 7.0 and 0.15 molar sodium chloride and was chromatographed on a 2.5×10 cm plastic column of QAE cellulose previously equilibrated with the same buffer. All of the AHF was bound under these conditions. Referring now to FIG. 3, when the unbound protein (16) had been washed through with 0.15 M NaCl, a step gradient of 0.20 M NaCl in the same buffer was run, an additional peak (18) of protein containing little or no AHF was eluted. Finally, a linear gradient of 180 ml from 0.20-1.0 M NaCl was run at 17 ml per hour. An additional peak (20) of protein was eluted, and towards the end of this peak, the AHF activity eluted in a fairly sharp peak (14) starting at around 0.3 M NaCl. The protein was pooled according to the AHF activity. Unbound proteins are indicated at 24 in FIG. 5 (SDS polyacrylamide gel electrophoresis [Laemmli] in a 6% gel); protein eluted with 0.2 N NaCl is represented at 26; and the peak at 28 was eluted at 0.2 M NaCl.

Figure 5:
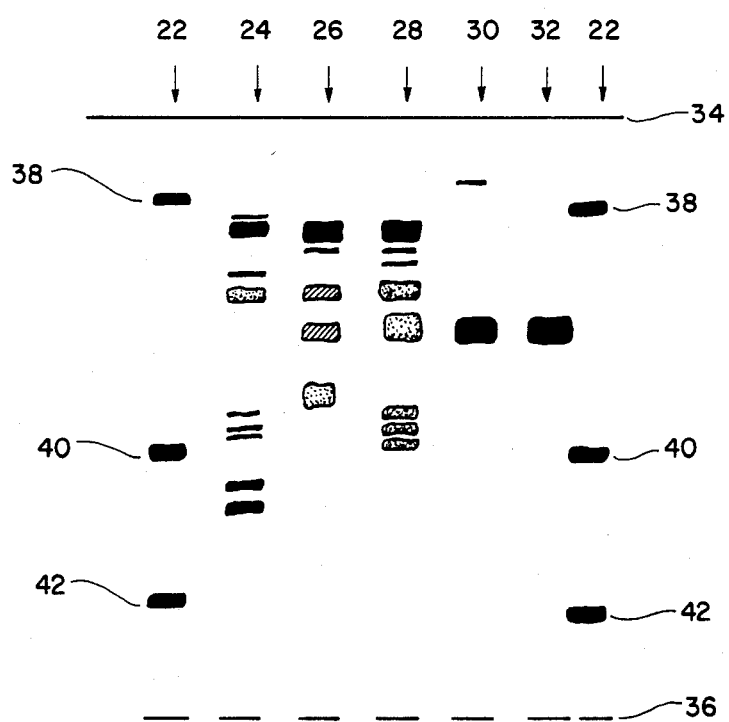
FIG. 5 is a depiction of the results of the SDS polyacrylamide gel electrophoresis (Laemmli, Nature, 277, 680–685, 1970, incorporated herein by reference) in a 6% gel on preparations produced in accordance with the invention.

The AHF preparation so-produced exhibited homogeneity (30) on SDS polyacrylamide gel electrophoresis (Laemmli) in a 6% gel (FIG. 5). The specific activity of this preparation was about 5,000 units of AHF activity per mg of protein, representing a 350,000 fold purification over source plasma. A 10% overall recovery from the commercial AHF concentrate was realized.

Figure 4:
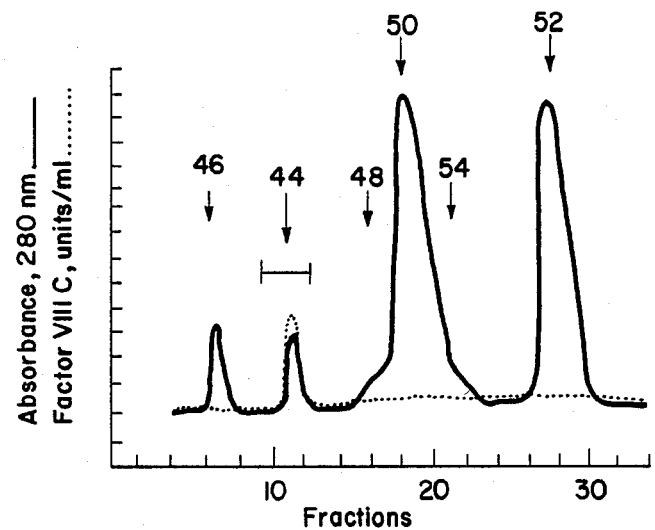

(4) The pooled fraction from step (3) was concentrated prior to high performance liquid chromatography (HPLC). HPLC was carried out on a Beckman TSK 4000 1×30 cm column at 40 psi, flow rate of 0.5 ml/hour. The profile is shown in FIG. 4. The AHF eluted coincident with the second peak (44), intermediate between the elution positions of IgM (MW 890,0000) and IgG (MW 160,000). The two largest peaks 50 and 52 do not contain AHF activity and have not been characterized. Peak 54 represents *bovine serum albumin* (BSA). In FIG. 4, arrows at 46, 48, and 54 represent elution volumes of marker proteins of known molecular weights in parallel runs: 46=1 gM (MW 890,000) and 48=IgG (MW 160,000).

Referring to FIG. 5, the AHF pool from step (4) above is essentially homogeneous (32) on SDS PAGE (Laemmli) in a 6% gel. This preparation has a specific activity of about 5000 AHF units per mg of protein representing a purification factor of 350,000 over source plasma. In FIG. 5 the origin for the SDS PAGE is represented at 34 and the ion front at 36. Column 22 represents myosin heavy chain (38) molecular weight 200,000, BSA (40) molecular weight 68,000, and ovalbumin (42) molecular weight 43,000.

The above operations and results are summarized in Table 2.

TABLE 2

| PURITICATION OF HUMAN AHF | | | | | |
|---|---|---|---|---|---|
| | Volume (ml) | Total Protein (mg) | Total Activity (units) | Specific Activity (units/mg) | Yield (%) | Purification (x-fold) |
| Plasma | — | — | — | 0.014 | — | 1 |

TABLE 2-continued

| | PURIFICATION OF HUMAN AHF | | | | | |
|---|---|---|---|---|---|---|
| | Volume (ml) | Total Protein (mg) | Total Activity (units) | Specific Activity (units/mg) | Yield (%) | Purification (x-fold) |
| Koate ® | 250 | 12,580 | 11,000 | 0.87 | 100 | 62 |
| Biogel A-15 M ammonium sulfate dialysis | 22 | 318 | 9,469 | 29.8 | 86 | 2,126 |
| $Ca^{++}$ dissociation Sepharose CL-4B dialysis | 110 | 13.2 | 6,850 | 519 | 62 | 37,067 |
| QAE cellulose | 29.5 | 0.28 | 1,396 | 4,986 | 12.7 | 356,122 |

All values represent the average of two preparations.

We claim:

1. A method for preparing a highly purified, essentially homogeneous Antihemophilic Factor concentrate, comprising the steps of:
    (a) obtaining an Antihemophilic Factor concentrate which is totally or partially free from prothrombin complex proteins, fibrinogen, and albumin,
    (b) subjecting the Antihemophilic Factor concentrate to a separation on the basis of Stokes radius to separate Antihemophilic Factor of an apparently high Stokes radius value from other proteins,
    (c) treating the Antihemophilic Factor concentrate to change the effective Stokes radius of the Antihemophilic Factor molecule to an apparently low value,
    (d) subjecting the Antihemophilic Factor concentrate to a separation on the basis of Stokes radius to separate Antihemophilic Factor of apparently low Stokes radius value from other proteins,
    (e) subjecting the Antihemophilic Factor concentrate to chromatography on an anion exchange medium to yield a highly purified, essentially homogeneous Factor VIII C characterized by a specific activity of at least 4000, being essentially free of fibrinogen and von Willebrand's protein, and single band electrophoretic mobility on SDS/PAGE at an apparent molecular weight around 100,000 daltons.

2. The method of claim 1 wherein the separation in step (b) or step (d) is accomplished by subjecting the Antihemophilic Factor concentrate to gel permeation chromatography on cross-linked agarose or cross-linked polyacrylamide.

3. The method of claim 1 wherein the separation in step (b) or step (d) is accomplished by subjecting the Antihemophilic Factor concentrate to controlled pore glass bead chromatography.

4. The method of claim 1 wherein the separation in step (b) or step (d) is accomplished by sucrose density gradient ultrafiltration.

5. The method of claim 1 wherein the Antihemophilic Factor concentrate in step (c) is treated with a source of divalent cations in an amount of about 5-10 parts by volume of Antihemophilic Factor concentrate per part of a solution of about 1-3 M in divalent cations.

6. A highly purified, essentially homogenous Antihemophilic Factor concentrate produced by the method of claim 1.

7. An essentially homogeneous, biologically active protein material characterized as follows:
    (a) procoagulant activity of at least about 4,000 AHF units per mg of protein;
    (b) essentially free of fibrinogen, fibronectin, von Willebrand's protein, and vitamin K-dependent coagulation factors; and
    (c) single-band electrophoretic mobility wherein essentially all AHF activity is found in said single band indicative of a single protein having an apparent molecular weight on SDS PAGE of about 100,000.

8. Material of claim 7 which contains less than about 1% combined of Factors II, VII, IX, and X, fibrinogen, albumin, fibronectin and von Willebrand factor.

9. An Antihemophilic Factor according to claim 7 having essentially no effect in a non-activated partial thromboplastin time assay.

10. The material of claim 7 wherein the ratio of Antihemophilic Factor to Antihemophilic Factor antigen is about 50:1 or greater.

* * * * *